United States Patent
Kaplan

(10) Patent No.: US 8,277,842 B1
(45) Date of Patent: Oct. 2, 2012

(54) ENTERIC-COATED HT-2157 COMPOSITIONS AND METHODS OF THEIR USE

(75) Inventor: Alan P Kaplan, San Diego, CA (US)

(73) Assignee: Dart NeuroScience (Cayman) Ltd., Grand Cayman (KY)

( * ) Notice: Subject to any disclaimer, the term of this patent is extended or adjusted under 35 U.S.C. 154(b) by 0 days.

(21) Appl. No.: 13/354,428

(22) Filed: Jan. 20, 2012

(51) Int. Cl.
*A61K 9/22* (2006.01)
*A61K 9/20* (2006.01)
*A61K 9/00* (2006.01)

(52) U.S. Cl. ......... 424/468; 424/400; 424/464; 424/474

(58) Field of Classification Search ........................ None
See application file for complete search history.

(56) References Cited

U.S. PATENT DOCUMENTS

| | | |
|---|---|---|
| 7,642,281 B2 | 1/2010 | Blackburn |
| 2004/0082615 A1 | 4/2004 | Konkel et al. |
| 2004/0102507 A1 | 5/2004 | Konkel et al. |
| 2004/0110821 A1 | 6/2004 | Konkel et al. |
| 2005/0192337 A1 | 9/2005 | Jubian et al. |
| 2007/0135509 A1 | 6/2007 | Blackburn et al. |
| 2007/0135510 A1 | 6/2007 | Blackburn et al. |
| 2008/0039496 A1 | 2/2008 | Blackburn et al. |
| 2011/0212156 A1* | 9/2011 | Chang et al. .................. 424/443 |

FOREIGN PATENT DOCUMENTS

| | | |
|---|---|---|
| WO | 2004014307 A2 | 2/2004 |
| WO | 2004014376 A1 | 2/2004 |
| WO | 2004014854 A1 | 2/2004 |
| WO | 2004014855 A1 | 2/2004 |
| WO | WO 2004014854 A1 * | 2/2004 |
| WO | 2009086532 A1 | 7/2009 |
| WO | 2010009453 A1 | 1/2010 |

OTHER PUBLICATIONS

Seifert et al., Toxicology 83, 49-59 (1993).
Sebestovfi et al., Toxicology 92, 27-38 (1994).
Kaleagasioglu et al., Toxicology 97, 123-131 (1995).
Kolakowski et al., J. Neurochem. 71:1 2239-225 (1998).
Swanson et al., Proc. Natl. Acad. Sci. USA 102, 17489-17494 (2005).
Ögren et al., CNS Drugs 20, 633-654 (2006).
Ash et al., Regul. Pept. 166, 59-67 (2010).
Mitsukawa et al., Cellular and Molecular Life Sciences 65, 1796-1805 (2008).
Konkel et al., J. Med. Chem. 49, 3757-3758 (2006).

* cited by examiner

*Primary Examiner* — Anand Desai
*Assistant Examiner* — Melissa Mercier
(74) *Attorney, Agent, or Firm* — Don J. Pelto, Esquire; Sheppard, Mullin, Richter & Hampton LLP

(57) ABSTRACT

Drug compositions comprising the compound HT-2157 and their therapeutic uses, including the treatment of CNS disorders and cognitive impairments and the modulation of cognitive function, are disclosed. More particularly, the present invention relates to enteric-coated formulations comprising HT-2157 that reduce the appearance of clinically relevant methemoglobinemia relative to administration of non-enteric-coated formulations comprising HT-2157.

20 Claims, No Drawings

ENTERIC-COATED HT-2157 COMPOSITIONS AND METHODS OF THEIR USE

APPLICATION DATA

This is an original, non-provisional utility patent application.

FIELD OF THE INVENTION

The present invention relates to drug compositions comprising the compound HT-2157 and their therapeutic uses, specifically in subjects, and more specifically in humans, including the treatment of CNS disorders and cognitive impairments and the modulation of cognitive function. More particularly, the present invention relates to enteric-coated formulations comprising HT-2157 that reduce appearance of clinically relevant methemoglobinemia relative to administration of non-enteric-coated formulations comprising HT-2157.

BACKGROUND OF THE INVENTION

HT-2157 (also called SNAP 37889 or SNEC-2) is an indolone-derived compound (1,3-dihydro-1-phenyl-3[[3-trifluoromethyl)phenyl]imino]-2H-indol-2-one) having the following structure:

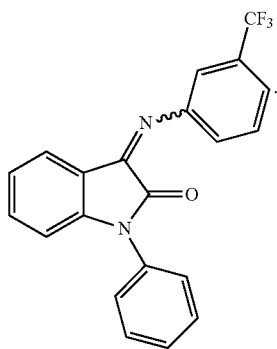

In laboratory studies, HT-2157 has been found to be a highly potent and selective antagonist of the Galanin 3 receptor (GalR3). See, e.g., Swanson et al., Proc. Natl. Acad. Sci. USA, 102, 17489-1494, 2005. GalR3 is one of three G-protein-coupled receptors—the other two being GalR1 and GalR2—that bind the peptide galanin. By inhibiting adenylate cyclase, galanin binding to GalR3 can reduce cAMP levels—a decrease that can be antagonized by HT-2157. See, e.g., Kolakowski et al., J. Neurochem. 71, 2239-2251, 1998.

Galanin is a neurotransmitter involved in a variety of peripheral and central physiological and pathophysiological processes, including gastrointestinal motility, cardiovascular contraction, neuroendocrine function, feeding behavior, pain perception, learning, memory, anxiety, and depression. For a review, see Mitsukawa et al., EXS 102, 7-23, 2010. The three galanin receptors are distributed in numerous areas of the CNS, including those associated with mood, memory, emotion, and pain. Consistent with these observations, studies of HT-2157 in cellular and animal models have shown multiple effects of this compound on function and pathology of the nervous system:

WO 09/086,532 relates to the use of neurite outgrowth assays as a general screen for compounds, including HT-2157, which can enhance and improve memory function.

US 2008/003946 relates to the administration of GalR3 antagonists to modulate neurite outgrowth. Such antagonists include HT-2157 and the E/Z isomers or mixtures thereof. The antagonists can be administered in single or divided doses or in sustained release forms, depending on numerous factors, including the particular symptoms and effect desired.

U.S. 2004/0110821 and WO 04014376 each relate to pyrimidine and indolone derivatives (including HT-2157) that are selective antagonists for the GAL3 receptor. Each describes a method of treating an affective disorder with compositions that can include a pharmaceutically acceptable carrier and a therapeutically effective amount of the selective antagonist. The composition may be in solid form and include lubricants, glidants, and binders.

U.S. 2005/0192337 relates to processes for preparing the HT-2157 compound.

WO 10/009,453 relates to methods and systems of evaluating, identifying, or assessing the effectiveness of memory agents and training protocols in subjects, including macaques and humans. The memory agents can be formulated as a solution, suspension, emulsion, or lyophilized powder, in association with a pharmaceutically acceptable parenteral vehicle.

U.S. 2007/0135509 and U.S. 2007/0135510 each relate to treating cognitive impairments with several different categories of compounds, including HT-2157. Solid forms of compositions suitable for oral administration include pills, capsules, granules, tablets, and powders.

US 2004/0102507 relates to methods for treating depressive and anxiety disorders with indolone compounds, including HT-2157. It further relates to pharmaceutical compositions, including solid forms or liquid forms, which combine such antagonists with a pharmaceutically acceptable carrier.

WO 04/014307 relates to GalR3 antagonists in the treatment of neuropathic pain and cognitive disorders. Such antagonists comprise indolines, including HT-2157. Solid carriers for use with such antagonists can include endogenous carriers (e.g. nutrient or micronutrient carriers), flavoring agents, lubricants, solubilizers, suspending agents, fillers, glidants, and compression aids U.S. Pat. No. 7,642,281 relates to methods for treating cognitive impairments with various compounds, including the indolone compound HT-2157. The indolone compounds can be formulated as capsules, including powder-filled hard gel capsules, as well as suppositories, creams, inhalants, or transdermal patches.

WO 04/014855 relates to crystalline and amorphous forms of HT-2157 and processes for their preparation. It is further directed to pharmaceutical compositions, including those comprising HT-2157, which are useful in treating depression, anxiety, and other CNS disorders. Solid carriers for use in such compositions include endogenous carriers (e.g. nutrient or micronutrient carriers), flavoring agents, lubricants, suspending agents, fillers, glidants, compression aids, binders or tablet-disintegrating agents.

WO 04/014854 and U.S. 2004/0082615 each relate to treating depression or anxiety with various categories of compounds, including the indolone compound HT-2157. Corresponding pharmaceutical compositions can include HT-2157, along with solid carriers, such as endogenous carriers, encapsulating materials, and powder mixtures.

Ash et al. (Regul. Pept. 166, 59-67, 2010) relates to behavioral studies in rats treated with HT-2157 (SNAP 37889) to evaluate a possible association between galanin and alcohol. Such studies included tests for anxiety and operant self-administration of ethanol.

Konkel et al. (J. Med. Chem. 49, 3757-3758, 2006) relates to a series of 3-imino-2-indolines as high-affinity antagonists of the galanin GAL3 receptor. The antagonists, which include HT-2157, showed high selectivity for GalR3 over a broad panel of targets, including GAL1 and GAL2.

Oegren et al. (CNS Drugs 20, 633-654, 2006) relates generally to the pathophysiology of mood disorders, including the observation that GalR3 receptor antagonists, such as HT-2157, can cross the blood-brain barrier after systemic administration and show antidepressant-like activity in several animal models.

Swanson et al. (Proc. Natl. Acad. Sci. USA 102, 17489-17494, 2005) relates to the use of behavioral, neurochemical, and electrophysiological approaches to investigate anxiolytic- and antidepressant-like effects following acute administration of GalR3-selective antagonists, including HT-2157 (SNAP 37889).

In summary, numerous studies have uncovered a role of GalR3 in modulating function and dysfunction in the nervous system, and they have uniformly disclosed and relied upon the HT-2157 compound itself or conventional HT-2157 formulations. As disclosed in the instant application, however, such conventional formulations have proven unsuitable for therapeutic use in humans, giving rise to significant and previously unreported safety issues. The present application discloses alternative HT-2157 compositions, which utilize an enteric coating, that overcome these safety issues.

SUMMARY OF THE INVENTION

In one aspect, the present disclosure relates to a composition that includes a solid dosage form comprising a therapeutically effective amount of HT-2157 and an enteric coating, wherein HT-2157 has the following structure:

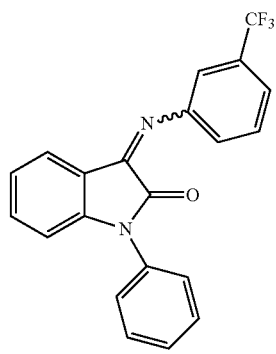

In some embodiments, administration of the composition to a subject reduces appearance of clinically relevant methemoglobinemia or results in a lower increase in percent of methemoglobin, relative to administration of a non-enteric coated composition comprising the same amount of HT-2157. In a specific aspect, administration of the compositions of the present invention increases methemoglobin levels to less than about 3 percent, or to less than about 1.5 percent. In some embodiments, the composition with an enteric coating provides greater bioavailability of HT-2157, compared to the composition without an enteric coating.

The enteric coating of the composition may, in one embodiment, comprise a methacrylic polymer, and the composition may further comprise one or more excipients, such as a diluent, binder, surfactant, glidant, or lubricant.

In certain embodiments, the composition remains stable after 1 year of storage at 25° C./60% R.H or after 6 months of storage at 40° C./75% R.H The present disclosure also relates to a method comprising administration of any of the compositions of the present invention, wherein the administration reduces appearance of clinically relevant methemoglobinemia or results in a lower increase in percent of methemoglobin, relative to administration of a non-enteric coated composition comprising the same amount of HT-2157.

In still another aspect, the present disclosure relates to a method of administering any of the compositions of the present invention to treat neuropathic pain or a CNS disorder in a subject in need thereof. In specific embodiments, the CNS disorder is depression or anxiety.

In yet another aspect, the present disclosure relates to a method of treating a cognitive impairment. In a specific embodiment, the method comprises the steps of: providing cognitive training to an animal in need of treatment of a cognitive impairment under conditions sufficient to produce an improvement in performance of a cognitive function whose deficit is associated with the cognitive impairment; administering a compositions of the present invention to the animal in conjunction with cognitive training; repeating the providing and administering steps one or more times; and (d) reducing the number of training sessions sufficient to produce the improvement in performance, relative to improvement in performance produced by cognitive training alone.

In a specific aspect of the methods, administering the compositions of the present invention reduces appearance of clinically relevant methemoglobinemia or results in a lower increase in percent of methemoglobin, relative to administration of a non-enteric coated composition comprising the same amount of HT-2157. In another aspect, the cognitive impairment includes a memory impairment.

Other features and advantages of the invention will become apparent from the following detailed description. It should be understood, however, that the detailed description and the specific examples, while indicating specific embodiments of the invention, are given by way of illustration only, because various changes and modifications within the spirit and scope of the invention will become apparent to those skilled in the art from this detailed description.

DETAILED DESCRIPTION OF THE INVENTION

Unless otherwise defined, all technical and scientific terms used herein have the same meaning as commonly understood by one of ordinary skill in the pharmaceutical arts. Although methods and materials similar or equivalent to those described herein can be used in the practice or testing of the present invention, suitable methods and materials are described herein. All publications, patent applications, patents, and other references, including product descriptions, clinical studies, and protocols, mentioned in this Application are incorporated by reference in their entirety. In addition, the materials, methods, and examples are illustrative only and are not intended to be limiting.

Reference is made to standard textbooks of molecular biology and pharmaceutics that contain definitions and methods and means for carrying out basic techniques, which may be encompassed by the present invention. See, e.g., Current Protocols in Pharmacology, Enna et al. (eds.), John Wiley and Sons, Inc., Hoboken, N.J. (2011), Current Protocols in Molecular Biology, Ausubel et al. (eds.), John Wiley & Sons, Inc., Hoboken, N.J. (2011), Current Protocols in Cell Biology, Bonifacino et al. (eds.), John Wiley & Sons, Inc.: Hoboken, N.J. (2011); Current Protocols in Neuroscience, Gerfen et al. (eds.), John Wiley & Sons, Inc., Hoboken, N.J. (2011); and the various references cited therein.

DEFINITIONS

The terms "comprising" and "including" are used herein in their open, non-limiting sense.

As used herein, the terms "a," "an," and "the" are to be understood as meaning both singular and plural, unless explicitly stated otherwise. Thus, "a," "an," and "the" (and grammatical variations thereof where appropriate) refer to one or more.

As used herein, the term "about" or "approximately" means within an acceptable range for a particular value as determined by one skilled in the art, and may depend in part on how the value is measured or determined, e.g., the limitations of the measurement system or technique. As used herein, the term "about," when located before a dosage amount or dosage range of a specific ingredient, refers to an amount or range closely above or closely below the stated amount or range that does not manifestly alter the therapeutic effect of the specific ingredient from the stated amount or range and is meant to encompass at least all equivalents of that amount. For example, "about" can mean a range of up to 20%, up to 10%, up to 5%, or up to 1% or less of a given value. Alternatively, with respect to biological systems or processes, the term "about" can mean within an order of magnitude, within 5-fold, or within 2-fold of a value. Numerical quantities given herein are approximate unless stated otherwise, meaning that the term "about" or "approximately" can be inferred when not expressly stated The term "HT-2157" is synonymous with "SNAP 37889" and "SNEC-2."

The term "HT-2800" is synonymous with "SNAP 68582" and refers to an active metabolite of HT-2157 that is formed in humans and some animals and has the following structure:

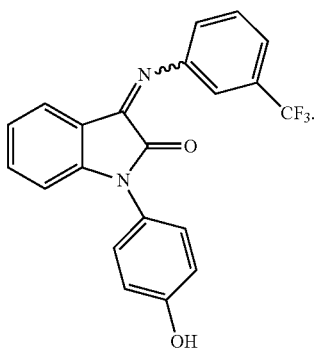

As used herein, a "subject" may be a vertebrate, in particular, a mammal, and more particularly, a human. A subject can also include a laboratory animal in the context of a clinical trial or screening or activity experiment. Thus, as can be readily appreciated by one of ordinary skill in the art, the compositions and methods of the present invention are particularly suited to administration to any vertebrate, particularly a mammal, and more particularly, a human.

As used in the present disclosure, the term "therapeutically effective amount" means an amount or dose of HT-2157 (or HT-2800) that is effective to ameliorate, delay, minimize, or prevent any symptom, behavior, or other event associated with a cognitive disorder, disease, or condition, or any other nervous system disorder, disease, or condition specified herein. Alternatively, a therapeutically effective amount is the amount of HT-2157 that is effective to improve one or more symptoms of a clinically significant disorder, disease, or condition in the individual.

As used herein, the terms "treat," "treatment," "treating" include:

(i) prophylactic treatment, which includes preventing and/or reducing the incidence of and/or ameliorating the effect and/or duration of a disease, disorder, or condition from occurring in subjects that may get, be exposed to and/or be predisposed to the disease, disorder or condition, but may not yet have been diagnosed as having it; or are diagnosed as having the disease, disease, or condition; or are at risk of developing such disease, disorder, or condition;

(ii) inhibiting the disease, disorder, or condition, i.e., delaying the onset of a disease, disorder, or condition; arresting further development or progression of a disease, disorder, or condition in a subject already suffering from or having one or more symptoms of the disease, disorder, or condition; or reducing the risk of a disease, disorder, or condition worsening;

(iii) relieving the disease, disorder, or condition, i.e., causing regression of the disease, disorder, or condition, or one or more of its symptoms.

As used herein, the phrase "pharmaceutically acceptable" refers to molecular entities and compositions that are generally regarded as "safe," e.g., that are physiologically tolerable and do not typically produce an allergic or similar untoward reaction, such as gastric upset, dizziness and the like, or other significant adverse events, when administered to a human. Preferably, as used herein, the term "pharmaceutically acceptable" means approved by a regulatory agency of the Federal or a state government of listed in the U.S. Pharmacopeia or other generally recognized pharmacopeia for use in animals, and more particularly in humans.

The term "carrier" refers to a diluent, adjuvant, excipient, or vehicle with which the compound is administered. In preferred embodiments of this invention, the carrier is a solid carrier. Suitable pharmaceutical carriers include those described in Remington: The Science and Practice of Pharmacy, 21st Ed., Lippincott Williams & Wilkins (2005).

The term "dosage form," as used herein, is the form in which the dose is to be administered to the subject or patient. The drug or supplement is generally administered as part of a formulation that includes nonmedical agents. The dosage form has unique physical and pharmaceutical characteristics. Dosage forms, for example, may be solid, liquid or gaseous. "Dosage forms," may include for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the terms "inactive," "inert," and "excipient" refer to any compound that is an inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

A "stable" composition is one in which the amount of active ingredient is not decreased by more than about 10% after about 1 year of storage at 25° C./60% RH or after about 6 months of storage at 40° C./75% RH.

The phrase "reduce the appearance of clinically relevant methemoglobinemia" means that methemoglobin levels in the blood are not increased to levels that cause significant health complications associated with the condition methemoglobinemia. In some embodiments, the phrase "reduce the appearance of clinically relevant methemoglobinemia" means methemoglobin levels in the blood are increased to less than about 3%, and in some embodiments to less than about 1.5%.

Pharmaceutical Compositions

The present invention is based partly upon the discovery that administration of the compound HT-2157 or conventional HT-2157 pharmaceutical compositions can result in methemoglobinemia. This previously unreported observation presents a significant safety issue that must be addressed in order to utilize HT-2157 in therapeutic applications.

Accordingly, the present invention discloses alternative HT-2157 compositions with an enteric coating that reduce clinically relevant methemoglobin in a subject or result in a lower increase in percent of methemoglobin, relative to administration of a conventional, i.e., non-enteric coated, composition comprising the same amount of HT-2157.

In addition to an enteric coating, compositions of the present invention may also comprise one or more pharmaceutically acceptable carriers, including excipients, such as a diluent, binder, surfactant, glidant, or lubricant. The solid dosage forms disclosed herein may also be formulated with other pharmaceutically inactive components, including, but not limited to, disintegrants, colorants, flavoring agents, preservatives, and sorbents. The excipients of the present invention are well known to those of ordinary skill in the art, and details can be found, for example, in Handbook of Pharmaceutical Excipients, $5^{th}$ Ed., Rowe et al. (eds.), Pharmaceutical Press (2005); Remington: The Science and Practice of Pharmacy, 21st Ed., Lippincott Williams & Wilkins (2005); Current Protocols in Pharmacology, Enna et al. (eds.), John Wiley and Sons, Inc., Hoboken, N.J. (2011).

In a specific embodiment, the solid dosage forms are for oral administration. In preparing the composition in oral dosage form, any of the usual media may be utilized. Pharmaceutical acceptable carriers such as diluents, fillers, binders, surfactants, granulating agents, lubricants, disintegrating agents and the like may be used to prepare oral solids (e.g., powders, caplets, pills, tablets, capsules) and determination of workable proportions in any particular instance will generally be within the capability of the person skilled in the art. Fillers and excipients, for example, are commercially available from companies such as Aldrich Chemical Co., FMC Corp, Bayer, BASF, Alexi Fres, Witco, Mallinckrodt, Rhodia, ISP, and others. Controlled release forms may also be used. Given their ease in administration, caplets, tablets, pills, and capsules represent the most advantageous oral dosage unit form, in which case solid carriers are employed. If desired, tablets may be sugar coated.

In a specific mode of administration, the dosage forms may be swallowable, chewable or dissolvable. Swallowable compositions are well known in the art and are those that do not readily dissolve when placed in the mouth and may be swallowed whole without any chewing or discomfort. In a specific embodiment of the present invention, the swallowable compositions may have a shape containing no sharp edges and a smooth, uniform and substantially bubble free outer coating. The compositions of the present invention may be prepared using conventional methods and materials known in the pharmaceutical arts.

Enteric Polymers and Coatings

Enteric polymers used to coat pharmaceutical dosage forms include cellulose, vinyl, and acrylic derivatives. Enteric polymeric materials are primarily weak acids containing acidic functional groups, which are capable of ionization at elevated pH.

In some embodiments, the enteric coating coats a core of a solid dosage form disclosed herein and controls the location in the digestive tract where the active agent contained in the solid dosage form's core is released and absorbed. In certain embodiments, the enteric coating is in the form of one or more components selected from the group including polymers, fatty acids, waxes, shellac, plastics, and plant fibers.

In certain embodiments, the enteric coating comprises one or more of the following: acrylates and acrylate copolymers, including methacrylic acid/methacrylic acid methylester copolymer and methacrylic acid/ethyl acrylate copolymer; cellulose esters, including cellulose acetate phthalate, cellulose acetate trimellitate, and cellulose acetate succinate; hydroxypropyl methylcellulose phthalate; hydroxypropyl methylcellulose acetate succinate; polyvinyl derivatives, including polyvinyl acetate phthalate; and carboxymethyl ethyl cellulose. In some specific embodiments, the enteric coating includes one or more components sold under trade names, for example EMCOAT 120 N, MARCOAT 125, AQUACOAT CPD®, SEPIFILM™, AQUACOAT® ECD, METOLOSE®, SURETERIC®, AND EUDRAGIT®. In certain embodiments, the enteric coating may comprise colorants. In a specific embodiment, the enteric coating comprises a EUDRAGIT® polymer and a colorant, and is sold under the trade name ACRYL-EZE ORANGE®.

In some embodiments, the enteric coating may further comprise a plasticizer. In some embodiments, the plasticizer will influence, i.e., increase or decrease, the rate of dissolution of the enteric coating. In some embodiments, the plasticizer may be lipophilic. In other embodiments, the plasticizer may be hydrophilic.

In other embodiments, the plasticizer comprises one or more of the group including cetanol, triacetin, citric acid esters such as triethyl citrate, phthalic acid esters such as diethyl phthalate and dibutyl phthalate, dibutyl succinate, propylene glycol, polyethylene glycol (PEG), and oils and glycerides such as fractional coconut oil.

In still other embodiments, the dosage forms disclosed herein comprise pharmacologically inactive components or excipients. Acceptable pharmacologically inactive components or excipients will be recognized by those of skill in the art, and include diluents, binders or fillers, surfactants, glidants, lubricants, disintegrants, colorants, flavoring agents, preservatives, and sorbents.

Diluents and Fillers

In certain embodiments, the dosage form is a solid dosage form, which can include one or more diluents or fillers. In some embodiments, the diluents or fillers comprise one or more selected from the group consisting of microcrystalline cellulose, colloidal silicon dioxide, starches such as pregelatinized starch, calcium carbonate, confectioner sugar, calcium phosphate, calcium hydrogen phosphate dihydrate, ethyl cellulose, mannitol, magnesium carbonate, magnesium oxide, and sodium chloride.

Binders

In specific embodiments, solid dosage forms disclosed herein comprise one or more binders. In some embodiments, the binders comprise one or more selected from the group consisting of hydroxypropyl cellulose, hydroxypropyl methyl cellulose, sucrose, lactose, starches, cellulose, microcrystalline cellulose, cellulose ethers, methyl cellulose, xylitol, sorbitol, and maltitol, gelatin, polyvinylpyrrolidone, polyethylene glycol, acacia, alginate, sodium alginate, alginic acid, candelilla wax, carnuba wax, corn starch, copolyvidone, povidone, and polyethylene oxide.

Surfactants

In certain embodiments, solid dosage forms disclosed herein comprise one or more surfactants. In some embodiments, the surfactants comprise one or more selected from the group consisting of sodium lauryl sulfate and glyceryl monosterate Glidants In particular embodiments, solid dosage forms disclosed herein comprise one or more glidants. In some embodiments, the glidants comprise one or more selected from the group consisting of colloidal silicon dioxide, fumed silica, talc, and magnesium carbonate.

Lubricants

In certain embodiments, solid dosage forms disclosed herein comprise one or more lubricants. In some embodiments, the lubricants comprise one or more selected from the group consisting of minerals, such as talc and silica, and fats and fatty acids, such as vegetable stearin, magnesium stearate, stearic acid, calcium stearate, castor oil, glyceryl behenate, mineral oil, poloxamers, sodium lauryl sulfate, and sodium stearyl fumarate.

Moisture Barriers

In some embodiments, the dosage forms may include a moisture barrier coating. For example, granules may be coated with a moisture barrier film to impede, retard, or protect against the absorption of environmental moisture or vapor. Suitable moisture barrier coatings may include wax components or other compounds known to one skilled in the art, such as ethyl cellulose, hypromellose (hydroxypropyl methylcellulose), polyvinyl alcohol, acrylic polymers, or other polymers. Thus, in one aspect of the invention, the moisture barrier substantially impedes or retards the absorption of moisture into the solid dosage form, thereby increasing the stability of HT-2157.

Processes

The dosage forms disclosed herein may be manufactured by any acceptable or art-recognized method including but not limited to: granulation of the core components to form a tablet mix prior to core formation using dry granulation, wet granulation, low shear wet granulation, high shear wet granulation, and fluid bed granulation; granule lubrication; compression of the tablet mix in a tablet press to form the core; coating of the core with an enteric coating using coating pans, spray coating, fluid-bed coating, dry coating, and the like.

Application of the enteric coating to an HT-2157 composition can be accomplished by any method known in the art for applying enteric coatings. For example, but not by way of limitation, the enteric polymers can be applied using organic solvent based solutions contain from about 5 to 10% w/w for spray applications and up to about 30% 1/1 polymer for pan coatings. Solvents that are commonly in use include, but are not limited to, acetone, acetone/ethyl acetate mixtures, methylene chloride/methanol mixtures, and tertiary mixtures containing these solvents. In addition, some enteric polymers, such as methacrylic acid-methacrylic acid ester copolymers can be applied using water as a dispersant. The volatility of the solvent system must be tailored to present sticking due to tackiness and to prevent high porosity of the coating due to premature spray drying or precipitation of the polymer as the solvent evaporates.

Solid Dosage Forms

Solid dosage forms may include granules, pellets, beads, spheroids, a tablet, a minitablet, a microtablet, a capsule, granules in a capsule, pellets in a capsule, microtablets in a capsule, and minitablets in a capsule, each of which may be enteric coated.

In specific embodiments, the dosage form comprises beads of HT-2157. In one aspect, the beads of HT-2157 or a salt may be prepared by spraying inactive cores with a slurry or a solution of HT-2157 or a salt thereof optionally along with other pharmaceutically acceptable excipients and optionally coating the beads of HT-2157 or a salt thereof thus obtained with a moisture barrier, followed by enteric coating with pharmaceutically acceptable enteric polymers.

In another aspect, the beads of HT-2157 or a salt thereof may also be prepared by a process of extrusion-spheronization or marumerization and optionally coating the beads of HT-2157 or a salt thereof thus obtained with a moisture barrier followed by enteric coating with pharmaceutically acceptable enteric polymers.

In still another aspect, the beads of HT-2157 or a salt thereof may be prepared by adsorbing HT-2157 or a salt thereof on pharmaceutically acceptable adsorbent, processing the adsorbate into beads of HT-2157 or a salt thereof and optionally coating the beads of HT-2157 or a salt thereof thus obtained with a moisture barrier followed by enteric coating with pharmaceutically acceptable enteric polymers.

Spraying or adsorption can be carried out by a fluidized bed processor, glatt, spray dryer or by any other suitable coating techniques known in the art.

The inactive cores can be made up of one or more of saccharides or derivatives thereof such as polysaccharides, sugars such as mannitol, sorbitol, lactose, sucrose, maltodextrin, starches such as maize starch, rice starch, celluloses such as microcrystalline cellulose, sodium carboxymethyl cellulose, vegetable gums, waxes, and the like.

The adsorbate of HT-257 or a salt thereof can be processed into beads of HT-2157 or a salt thereof by extrusion-spheronization or marumerization or any other suitable technique known in the art.

The pharmaceutically acceptable adsorbents may be one or more of colloidal silicon dioxide, calcium silicate, magnesium aluminum silicate, porous ceramics, polypropylene foams, cellulose, cellulose derivatives, polyols, starches, pregelatinized starches, starch derivatives, modified starches, dextrins, maltodextrins, polydextroses, dextroses, calcium carbonate, calcium phosphate, or calcium sulfate.

The slurry or solution of HT-2157 or a salt thereof may include HT-2157 or a salt thereof suspended or dissolved in water, optionally along with other pharmaceutically acceptable excipients, such as hypromellose, hydroxypropyl cellulose, polyvinyl pyrrolidone, methacrylates and the like, and optionally with other pharmaceutically acceptable excipients. The slurry of HT-2157 or a salt thereof may be milled through a machine adapted for grinding suspensions in order to reduce the particle size of HT-2157. See Remington: The Science and Practice of Pharmacy, 21st Ed., Lippincott Williams & Wilkins (2005).

Methods

The present invention provides various methods relying on administration of HT-2157 compositions of the present invention to treat a central nervous system ("CNS") disorder. The term "disorder" is used interchangeably with "condition" or "disease." The present invention also provides methods to treat a cognitive deficit, such as an impairment in memory. In some embodiments, administration of a composition of the present invention is carried out in conjunction with a cognitive training protocol, as discussed below. In a specific aspect, these methods reduce the appearance of clinically relevant methemoglobinemia or result in a lower increase in the percent methemoglobin, relative to non-enteric compositions comprising the same amount of HT-2157.

Dosages

Optimal dosages to be administered may be determined by those skilled in the art and will depend on multiple factors, including the particular composition in use, the strength of the preparation, the mode and time of administration, and the advancement of the disease or condition. Additional factors may include characteristics on the subject being treated, such as age, weight, gender, and diet.

When used according to the compositions and methods of the present invention, the effective dose may be in the range of about 0.01 to 100 mg/kg, specifically about 0.01 to 10 mg/kg, more specifically, about 0.01 to 5 mg/kg, and even more specifically, about 0.5 to 5 mg/kg.

CNS and Cognitive Disorders

In certain embodiments, compositions of the present invention are used in methods for treating various disorders, including neuropathic pain and other CNS disorders. In specific embodiments, the CNS disorder is depression or anxiety.

In other embodiments, compositions of the instant invention are used in methods for treating a cognitive disorder. For the purposes of the present invention, the terms "cognitive impairment" and "cognitive disorder" are deemed to cover the same therapeutic indications, and are used interchangeably throughout this application.

Cognitive disorders reflect problems in cognition, i.e., the general processes by which knowledge is acquired, retained and used. Accordingly, cognitive disorders can encompass impairments in functions such as concentration, perception, attention, information processing, learning, memory, and/or language. Cognitive disorders can also encompass impairments in psychomotor learning, which include physical skills such as movement and coordination; disruptions in fine motor skills such as the use of precision instruments or tools; and deficits in gross motor skills, such as those engaged in dance, musical, and/or athletic performance.

Cognitive disorders can also encompass impairments in executive functions, which include abilities underlying the planning and execution of goal-oriented behaviors. Such abilities include flexibility, i.e., the capacity for quickly switching to the appropriate mental mode; anticipation and prediction based on pattern recognition; reasoning and problem-solving; decision making; working memory, i.e., the capacity to hold and manipulate internally or externally-derived information in real time; emotional self-regulation, including the ability to recognize and manage one's emotions for good performance; sequencing, such as the ability to dissect complex actions into manageable units and prioritize them in the right order; and self-inhibition, i.e., the ability to withstand distraction and internal urges.

Cognitive disorders commonly occur in association with CNS disorders (also referred to as CNS conditions or CNS diseases). CNS disorders include, but are not limited to, the following categories (which need not be mutually exclusive): (1) dementias, for example, those associated with Alzheimer's disease, Parkinson's disease, Huntington's disease, and other neurodegenerative diseases; (2) anxiety disorders, such as phobias, panic disorders, obsessive-compulsive disorder, generalized anxiety disorder, eating disorders, and posttraumatic stress disorder; (3) mood disorders, such as depression and bipolar disorder; (4) psychotic disorders, such as schizophrenia and delusional disorder; (5) developmental and genetic conditions affecting cognitive functions, such as autism spectrum disorders and mental retardation; (6) trauma-dependent losses of cognitive functions, such as memory, language, and motor impairments resulting from head trauma, stroke, hypoxia, viral infection (e.g., encephalitis), and alcohol abuse; (7) age-associated memory impairments, including mild cognitive impairment (MCI); and (8) learning disabilities, such as perceptual handicaps, dyslexia, and attention disorders.

In some cases, cognitive impairments can be a direct result of a CNS disorder. For example, impairments in speech and language may be a direct result of a stroke or head-injury that damages the brain regions controlling speech and language, as in aphasia. In other cases, cognitive impairments may be associated with a complex developmental or genetic syndrome, such as deficits in executive control that accompany autism or mental retardation.

Cognitive disorders can significantly impair social and occupational functioning, adversely impacting the autonomy and quality of life of the affected individual. An estimated four to five million Americans (about 2% of all ages and 15% of those older than 65) have some form and degree of cognitive impairment. Abrams et al., Merck Manual of Geriatrics, Whitehouse Station (NJ), Medical Services, 1995.

Cognitive Training

In some embodiments, the compositions of the instant invention are used in conjunction with cognitive training. Cognitive training protocols and the underlying principles are well known in the art. See, e.g., U.S. Pat. No. 7,868,015 (and references cited therein); Klingberg et al., J. Am. Acad. Child. Adolesc. Psychiatry 44, 177-186, 2005; Belleville et al., Dement. Geriatr. Cogn. Disord. 22, 486-499, 2006; Jaeggi et al., Proc. Natl. Acad. Sci. USA 105, 6829-6833, 2008; Lustig et al., Neuropsychol. Rev. 19, 504-522, 2009; Park and Reuter-Lorenz, Ann. Rev. Psych. 60, 173-196, 2009; Chem et al., Psychon. Bull. Rev. 17, 193-199, 2010; Klingberg, Trends Cogn. Sci. 14, 317-324, 2010; Owen et al., Nature 465, 775-778, 2010; Jaeggi et al., Proc. Natl. Acad. Sci. USA 108, 10081-10086, 2011.

Cognitive training protocols are directed to numerous cognitive dimensions, including memory, concentration and attention, perception, learning, planning, sequencing, and judgment. One or more protocols (or modules) underling a cognitive training program can be provided to a subject.

In some embodiments, the protocols can be used to treat, or rehabilitate, cognitive impairments in afflicted subjects. Such protocols may be restorative or remedial, intended to reestablish prior skills and cognitive functions, while other protocols may be focused on delaying or slowing cognitive decline due to neurological disease. Other protocols may be compensatory, providing a means to adapt to a cognitive deficit by enhancing function of related and uninvolved cognitive domains. In other embodiments, the protocols can be used to improve particular skills or cognitive functions in otherwise healthy individuals. For example, a cognitive training program might include modules focused on delaying or preventing cognitive decline that normally accompanies aging; here the program is designed to maintain or improve cognitive health.

In general, a cognitive training protocol (or module) comprises a set of distinct exercises that can be process-specific or skill-based: Process-specific training focuses on improving a particular cognitive domain such as attention, memory, language, or executive functions. Here the goal of cognitive training is to obtain a general improvement that transfers from the trained activities to untrained activities associated with the same cognitive function or domain. For example, an auditory cognitive training protocol can be used to treat a student with impaired auditory attention. At the end of training, the student should show a generalized improvement in auditory attention, manifested by an increased ability to attend to and concentrate on verbal information presented in class—and therefore to remember to write down and complete homework assignments.

Similarly, a cognitive training protocol may be directed to impaired executive function in an autistic subject, preventing the subject from carrying out instructions to complete an activity, such as making a meal, cleaning one's room, or preparing for school in the morning. Cognitive training allows the subject to focus his attention and concentration and as a result, complete the sequence of tasks required for such activities.

Skill-based cognitive training is aimed at improving performance of a particular activity or ability. Here the goal of cognitive training is to obtain a general improvement in the skill or ability. For example, a training protocol may focus on learning a new language, performing a musical instrument, or improving memory. The different exercises within such a protocol will focus on core components underlying skill. Modules for increasing memory, for example, may include tasks directed to the recognition and use of fact, and the acquisition and comprehension of explicit knowledge rules.

Some cognitive rehabilitation programs may rely on a single strategy (such as computer-assisted cognitive training) targeting either an isolated cognitive function or multiple functions concurrently. For example, the CogState testing method comprises a customizable range of computerized cognitive tasks able to measure baseline and change in cognitive domains underlying attention, memory, executive function, as well as language and social-emotional cognition. See, e.g., Yoshida et al., PLoS ONE 6, e20469, 2011; Frederickson et al., Neuroepidemiology 34, 65-75, 2010. Other cognitive rehabilitation programs may use an integrated or interdisciplinary approach. Cognitive training programs may involve computer games, handheld game devices, interactive exercises, and may employ feedback and adaptive models.

Augmented Cognitive Training

Cognitive training protocols generally require multiple training sessions to attain the desired benefits. This can be costly and time-consuming, deterring subject compliance and the realization of real world benefits that endure. These deficits underscore the need for methods to improve the efficiency of cognitive training.

The efficiency of cognitive training can be improved by administering certain agents (known as augmenting agents) in conjunction with cognitive training. Such augmenting agents have the ability to enhance CREB pathway function. More particularly, this method (known as augmented cognitive training or ACT) can decrease the number of training sessions required to improve performance of a cognitive function, relative to the improvement observed by cognitive training alone. (See, e.g., U.S. Pat. No. 7,868,015; U.S. Pat. No. 7,947,731; U.S. 2008/0051437).

In this regard, several recent investigations indicate that HT-2157 is such an augmenting agent. For example, injection or oral administration of HT-2157 has been shown to enhance 24-hour memory (long-term memory) in a standardized contextual fear conditioning task. See U.S. Pat. No. 7,642,281. In addition, intraperitoneal administration of HT-2157 has been shown to enhance 24 hour memory (long-term memory) in an object recognition task. See U.S. Pat. No. 7,642,281. In each of these tasks, the cyclic AMP response element binding protein (CREB) pathway is required for long-term memory formation. Indeed, the fear conditioning task was originally developed for evaluation of memory in CREB knock-out mice. Bourtchouladze et al., Cell 79, 59-68, 1994.

The enhancing effect of HT-2157 in these two tasks indicates that this compound enhances CREB pathway function and therefore can augment cognitive training. Accordingly, in certain embodiments, the methods of the present invention comprise administering an HT-2157 composition of the instant invention in conjunction with a cognitive training protocol. The phrase "in conjunction" means that HT-2157 enhances CREB pathway function during cognitive training.

In a particular embodiment, the method comprises the steps of: (a) providing cognitive training to a subject in need of treatment of a cognitive deficit under conditions sufficient to produce an improvement in performance by said animal of a cognitive function whose impairment is associated with said cognitive deficit; (b) administering an enteric-coated composition of the present invention to the animal in conjunction with said cognitive training; repeating steps (a) and (b) one or more times; and (d) reducing the number of training sessions sufficient to produce the improvement in performance, relative to the same improvement in performance produced by cognitive training alone.

In other embodiments, this method reduces appearance of clinically relevant methemoglobinemia or results in a lower increase in percent of methemoglobin in a subject, relative to administration of a non-enteric coated composition comprising the same amount of HT-2157.

In a specific aspect, the cognitive deficit treated by these methods is or includes a memory impairment, and more particularly, a defect in long-term memory.

EXAMPLES

The present disclosure will be further illustrated by the following non-limiting Examples. These Examples are understood to be exemplary only, and they are not to be construed as limiting the scope of the invention as defined by the appended claims.

Example 1

HT-2157 and Methemoglobinemia

Background

Methemoglobinemia is a disorder characterized by the presence of a higher than normal level of methemoglobin (metHb) in the blood. For a review, see Lee and Taraber, Medscape Emergency Medicine, Apr. 11, 2011; Lee and Ferguson, Medscape Emergency Medicine, Apr. 11, 2011. Methemoglobin is an oxidized form of hemoglobin that has a decreased affinity for oxygen, leading to an increased affinity of oxygen to other heme sites that results in an overall reduced ability to release oxygen to tissue. In healthy humans, the protective enzyme systems normally present in red blood cells maintain methemoglobin levels at less than 1 to 1.5 percent of the total hemoglobin. When methemoglobin levels are too high, tissue hypoxia can occur. Levels above 30% can result in multiple adverse consequences, including dyspnea, nausea, and tachycardia. Moreover, there is no known safe level of methemoglobin exposure above about 1 to 1.5 percent.

Methemoglobinemia can occur as either a hereditary or acquired condition. For a review, see Ashurst and Wasson, Del. Med. 83, 203-208, 2011. Hereditary methemoglobinemia has multiple causes, including congenital deficiencies in diaphorase 1 (NADH methemoglobin reductase) or pyruvate kinase—an essential cofactor for diaphorase 1; or the presence of an abnormal hemoglobin variant not amenable to reduction, such as hemoglobin M or hemoglobin H. Such hereditary forms are often associated with methemoglobin levels of 20-40 percent of total hemoglobin.

Acquired methemoglobinemia can result from exposure to certain drugs, metabolites, and toxins, which may accelerate the rate of formation of methemoglobin up to 1000-fold, overwhelming the protective enzyme systems and acutely increasing methemoglobin levels. Such exposure is typically associated with methemoglobin levels of about 5 to about 15%. Substances that may be associated with acquired methemoglobinemia include drugs and toxic substances, such as sodium nitrite, amyl nitrite, nitroglycerin, nitroprusside, silver nitrate, aniline dyes, acetanilid, phenacetin, sulfonamides, lidocaine, topical benzocaine, chlorate paraquat, and phenazopyridine.

Animal Studies

Numerous animal studies, including the following, show that administering HT-2157 (without an enteric coating) can increase the formation of methemoglobin in red blood cells, limiting its therapeutic potential. Such HT-2157 administration studies were carried out in several animal models, including rats, dogs (as well as mice). In this regard, the major human metabolite of HT-2157, HT-2800, was found in human, mouse, and monkey microsomes following incubation with the HT-2157 compound, but it was not detected in rat or dog microsomes or in plasma collected from dogs dosed with HT-2157.

Consequently, separate toxicokinetic studies directed to HT-2800 (without an enteric coating) were performed in rat and in dog, which is considered the more sensitive species. These studies demonstrated two types of hematological abnormalities: hemolytic anemia and methemoglobinemia, which appeared to be dose-dependent effects. In these studies, the non-toxic dose level for oral administration of HT-2157 over 28 days was 30 mg/kg/day for female rats, 100 mg/kg/day for male rats and 50 mg/kg/day for dogs (both sexes). Table 1 lists the mean $C_{max}$ and AUC values of HT-2157 in the plasma associated with these dosages:

TABLE 1

28-Day Oral Toxicity Studies with Non-enteric Coated HT-2157

| Species | Ref # | NOEL | NOEL | Duration of Dosing (days) | $C_{max}$ (ng/ml) | $AUC_{0-24}$ (ng · h/ml) |
|---|---|---|---|---|---|---|
| Rat-Male | 5 | 100 | 590 | 1 | 252 | 1376 |
| | | | | 28 | 442 | 1445 |
| Rat-Female | 5 | 30 | 177 | 1 | 77.8 | 235 |
| | | | | 28 | 109 | 283 |
| Dog-Male | 6 | 50 | 1000 | 1 | 99.0 | 676 |
| | | | | 28 | 87.1 | 550 |
| Dog-Female | 6 | 50 | 1000 | 1 | 162.2 | 571 |
| | | | | 28 | 103.7 | 799 |

NOEL: No effect level

Hemolytic anemia was observed in these studies, and there were decreases of approximately 4 to 21% in the following hematologic parameters: red blood cells (RBC), hemoglobin, hematocrit, and mean corpuscular hemoglobin concentration (MCHC). There were also increases of between 6 and 110% in the following parameters: platelet count, mean corpuscular volume (MCV) and red cell distribution width.

These findings indicate that a process of hemolytic anemia and compensatory hematopoietic response to anemia occurred in the animals. The hemolytic anemia was reversible upon discontinuation of drug treatment. In animals at high doses, there were also increases in methemoglobin of between 30 and 40% in treatment as compared to control animals. These increases resolved 1 to 2 weeks after discontinuation of dosing. Ninety-day studies with HT-2157 revealed statistically significant methemoglobin formation at 750 mg/kg/day for mice, 150 mg/kg/day for rats, and 30 mg/kg/day and higher for dogs.

Drug-related findings in repeat-dose animal toxicology studies conducted with non-enteric coated HT-2157 administered PO in mice for up to 3 months, rats for up to 1 year, and dogs for up to 9 months, and with non-enteric coated HT-2800 administered PO in rats for up to 6 months and in dogs for 9 months were restricted to dose-dependent shifts in hemoglobin fractions (methemoglobin, carboxyhemoglobin, oxyhemoglobin) and mild to moderate reversible hemolytic anemia with associated compensatory responses.

Example 2

Clinical Studies of HT-2157 Formulations

Uncoated Solid-Dosage Capsules

Subjects were administered single and repeated doses of a conventional non-enteric coated HT-2157 formulation, namely uncoated powder-filled capsules. Following administration of the HT-2157 powder capsules, elevated methemoglobin levels were seen in several subjects at dose levels ranging from 150 to 600 mg.

Enteric-Coated and Uncoated Liquid Gel Capsules Compositions and Administration

The results described here were based on oral administration of standard (uncoated) and enteric-coated formulations described in Table 2 and 3, respectively:

TABLE 2

Composition of HT-2157 (20 mg) Uncoated Liquid Capsules

| Component | Purpose | Percentage | Weight (mg/capsule) |
|---|---|---|---|
| HT-2157 | API | 3 | 20 |
| Cremophor RH 40 | Excipient | 32.3 | 215.4 |
| Vitamin E TPGS | Excipient | 64.7 | 431.6 |
| Capsugel ® Swedish Orange opaque Licaps size 0 capsules | Capsule | N/A | N/A |
| Total | | 100 | 667 |

N/A = not applicable

TABLE 3

Composition of HT-2157 (30 mg) Enteric-Coated Liquid Capsules

| Component | Purpose | Percentage | Weight (mg/capsule) |
|---|---|---|---|
| HT-2157 | API | 3.1 | 30.1 |
| Cremophor RH 40 | Excipient | 32.27 | 313 |
| Vitamin E TPGS | Excipient | 64.63 | 626.9 |
| Capsugel ® Swedish Orange opaque Licaps size 00EL capsules | Capsule | N/A | N/A |
| Total | | 100 | 667 |

Enteric-coat composition: Eudragit FCC D55 (95.24%) + Triethyl citrate (4.76%)
N/A = not applicable Two groups of subjects received a 120 mg dose of HT-2157 once-a-day for three days under fed conditions: One group received 20 mg standard (uncoated) HT-2157 gel capsules in an amount totaling 120 mg. The other group received 30 mg enteric-coated gel capsules in an amount totaling 120 mg.

Pharmacokinetics

Table 4 summarizes the accumulation of HT-2157 and HT-2800 in the two groups at the first and third day of dosing. After one-day and three days of dosing, exposures to HT-2157 and HT-2800 were much higher in the enteric capsule group than the uncoated capsule group. The bioavailability of HT-2157 in the gel capsules was therefore significantly increased in the presence of an enteric-coating.

TABLE 4

HT-2157 and HT-2800 Levels in Groups Receiving Uncoated and Enteric-Coated Gel Capsules (120 mg)

| Mean AUC | Uncoated | | Enteric-Coated | |
|---|---|---|---|---|
| (hr · ng/ml) | HT-2157 | HT-2800 | HT-2157 | HT-2800 |
| 0-24 h | 10.2 | 30.9 | 85.4 | 91.8 |
| 48-72 h | 13.4 | 42.2 | 180.3 | 211.6 |

Methemoglobin

Table 5 shows the methemoglobin responses associated with administration of the uncoated and enteric-coated HT-2157 gel capsules.

TABLE 5

Methemoglobin Levels Reached in Groups Receiving Uncoated and Enteric-Coated Capsules (120 mg) Mean Peak Levels of Methemoglobin (%)

| Uncoated | Enteric-Coated |
|---|---|
| 2.53 | 0.58 |

The mean peak level of methemoglobin in the uncoated group was 2.53%—above the normal upper limit of 1.5%. On an individual basis, 3 out of 4 subjects in the uncoated group had methemoglobin levels above the normal upper limit (1.5%).

In contrast, the mean peak level of methemoglobin in the enteric coated group was only 0.58%—well below the normal upper limit. Moreover, this group showed very little variation in methemoglobin values after a small rise between the 0 and 12 hour time points, and no individual in this group showed methemoglobin levels above the normal range (0 to 1.5%).

In sum, these results indicate that enteric-coating of oral formulations of HT-2157 may mitigate or prevent the formation of clinically relevant levels of methemoglobin caused by HT-2157. Indeed, even though exposures to HT-2157 and HT-21800 were much higher in the enteric coated group than the uncoated group (Table 4), the subjects in the enteric coated group showed no unsafe (clinically relevant) levels of methemoglobin (Table 5).

Enteric-Coated, Solid-Dosage Tablets

Twenty normal, healthy female volunteers were enrolled in a double-blind, single center, placebo-controlled, randomized, study to evaluate the pharmacokinetic and safety profiles of single doses (25, 50, 150, and 200 mg) of an enteric-coated tablet formulation of HT-2157.

Compositions and Administration

Tables 6 and 7 list the components of enteric-coated HT-2157 tablets and enteric-coated placebo tablets, respectively.

TABLE 6

Composition of Enteric-Coated HT-2157 Tablets

| Component | Purpose | Weight (mg/tablet) |
|---|---|---|
| HT-2157 (milled) | API | 25.0 |
| Microcrystalline Cellulose and Colloidal Silicon Dioxide (Prosolv SMCC 90LM) | Diluent | 191.0 |
| Pregelatinized Starch, Starch 1500 | Diluent | 60.0 |
| Hydroxypropyl Cellulose, Klucel EF | Binder | 15.0 |
| Sodium Lauryl Sulfate, Stepanol ® | Surfactant | 6.0 |
| Colloidal Silicon Dioxide (Cab-o-Sil M-5P) | Glidant | 1.5 |
| Magnesium Stearate (HyQual ®) | Lubricant | 1.5 |
| Acryl-eze Orange | Enteric coating | 25.0 |

TABLE 7

Quantitative Composition of Enteric-Coated Placebo Tablets

| Component | Weight (mg/tablet) |
|---|---|
| Microcrystalline Cellulose and Colloidal Silicon Dioxide (Prosolv SMCC 90 LM) | 208.4 |
| Pregelatinized Starch, Starch 1500 | 65.5 |
| Hydroxypropyl Cellulose, Klucel EF | 16.4 |
| Sodium Lauryl Sulfate, Stepanol ® | 6.5 |
| Colloidal Silicon Dioxide (Cab-o-Sil M-5P) | 1.6 |
| Magnesium Stearate (HyQual ®) | 1.6 |
| Acryl-eze Orange (Enteric Coating) | 48.0 |
| Total | 348 |

The subjects were divided into 4 cohorts. Each cohort had five members, four receiving the HT-2157 tablet and one receiving a placebo. The subjects in each cohort were randomized to receive 25 mg enteric-coated tablets of HT-2157 (or matching placebo tablets) in amounts totaling 25, 50, 150, and 200 mg, respectively, under fasting conditions.

Pharmacokinetics

In the 25 mg and 50 mg groups, HT-2157 plasma concentrations were generally below the limit of quantification. In the 150 mg and 200 mg dose groups, comparable mean AUC, CL/F and $T_{1/2}$ values for HT-2157 were observed. The mean $C_{max}$ values for HT-2157 were greater in the 200 mg group than in the 150 mg group (5.03 vs. 2.71 ng/ml), and mean $T_{max}$ values occurred later in the 200 mg group than in the 150 mg group (8.75 vs. 6.0 hours).

Mean plasma exposures of HT-2800 were comparable in the 25 and 50 mg dose groups. Although formal linear regression analysis was not performed, visual comparisons of mean AUC and $C_{max}$ data for HT-2800 suggest that plasma exposures increase proportionally with the HT-2157 dose across the dose range of 50 to 200 mg. The mean $T_{1/2}$ values for HT-2800 varied, ranging from approximately 11 hours (200 mg group) to 31 hours (50 mg group). At the two highest dose levels, the mean $T_{max}$ values for HT-2800 were comparable to those of the parent.

Table 8 summarizes the accumulation of HT-2157 and HT-2800 in the tablet cohorts at 3 days following a single dose:

TABLE 8

HT-2157 and HT-2800 Levels in
Enteric-Coated Tablet Cohorts

| Single Dose (mg) | HT-2157 | HT-2800 |
|---|---|---|
| | Mean $AUC_{0-72}$ (hr · ng/ml) | |
| 25 | 0 | 23.7 |
| 50 | 1.21 | 23.6 |
| 150 | 53.9 | 97.28 |
| 200 | 48.8 | 124.84 |

Methemoglobin

All of the individual methemoglobin values were below 1.5% in the active and placebo groups. No subjects developed methemoglobinemia.

In sum, the results from this study indicate that the plasma levels of drug were comparable with what had been seen using non-enteric coated formulations, but there was no indication of methemoglobinemia in any of the trial participants.

Stability

The 12-month stability results for 25 mg enteric-coated tablets stored under standard and accelerated conditions are listed in Tables 9 and 10, respectively:

TABLE 9

Stability Results for 25 mg HT-2157 Enteric Coated Tablets:
25° C./60% RH

| | Initial | 1 Month | 3 Months | 6 Months | 12 Months |
|---|---|---|---|---|---|
| HPLC Assay (90.0%-100.0%) | 97.1 | 95.1 | 95.4 | 93.7 | 95.9 |
| Total Impurities | 2.7 | 2.9 | 2.8 | 3.0 | 3.4 |
| TFMA | 0.96 | 1.06 | 0.99 | 1.06 | 1.22 |
| PIT | 1.67 | 1.80 | 1.74 | 1.76 | 1.96 |
| DPA | <0.1 | <0.01 | <0.01 | <0.01 | <0.01 |
| HT-2860 | <0.1 | <0.01 | <0.01 | <0.01 | 0.09 |
| Unknown | 0.09 | 0.07 | 0.10 | 0.17 | 0.12 |

[3]TFMA = m-trifluoromethylaniline
[2]PIT = 1-phenylisatin
[3]DPA = diphenylamine

TABLE 10

Stability Results for 25 mg HT-2157 Enteric Coated Tablets:
40° C./75% RH

| | Initial | 1 Month | 3 Months | 6 Months |
|---|---|---|---|---|
| HPLC Assay (90.0%-100.0%) | 97.1 | 93.5 | 93.6 | 92.1 |
| Total Impurities | 2.7 | 3.7 | 3.4 | 3.6 |
| TFMA[1] | 0.96 | 1.39 | 1.32 | 1.50 |
| PIT[2] | 1.67 | 2.17 | 1.81 | 1.61 |
| DPA[3] | <0.1 | <0.01 | <0.01 | <0.1 |
| HT-2860 | <0.1 | 0.05 | 0.18 | <0.38 |
| Unknown | 0.09 | 0.07 | 0.10 | 0.15 |

[3]TFMA = m-trifluoromethylaniline
[2]PIT = 1-phenylisatin
[3]DPA = diphenylamine These data show that the 25 mg enteric-coated tablets meet the HPLC Assay specifications (90.0%-100.0%) at 25° C./60% RH and 40° C./75% RH. At the end of each set of storage conditions, the amount of HT-2157 was not decreased by more than 10%.

Example 3

Pharmacokinetic and Safety Data Following Administration of Enteric-Coated Versus Non-Enteric Coated HT-2157 Formulations This study is a randomized double-blind, placebo-controlled, multiple dose evaluation of the safety, tolerability, and pharmacokinetics of orally-administered, enteric-coated versus non-enteric coated HT-2157 solid-dosage formulation in healthy volunteers.

The study comprises two cohorts: Group I and Group II. Each cohort has ten members, eight receiving a HT-2157 solid-dosage formulation and two receiving a placebo tablet. Subjects in cohort 1 are randomized to receive an enteric-coated, solid-dosage HT-2157 (or matching placebo) tablet in single doses for 21 days. Subjects in cohort 2 are randomized to receive a non-enteric coated HT-2157 (or matching placebo) tablet in single doses for 21 days. Following administration of the enteric-coated and non-enteric coated formulations, multiple parameters, including pharmacokinetics (PK) and safety data are evaluated.

Pharmacokinetics and Methemoglobin

The results include the observation that at the same dosage (125 mg), the $C_{MAX}$ is higher in subjects receiving the enteric-coated HT-2157 formulation versus the non-enteric coated HT-2157 formulation. However, despite their higher exposure to HT-2157, subjects in the enteric coated group show no clinically relevant methemoglobinemia. In all subjects receiving the enteric-coated formulation, the levels of methemoglobin remain below 1.5%.

Example 4

Therapeutic Administration of Enteric-Coated HT-2157 Formulations

This trial comprises a randomized, double-blind, placebo-controlled, multiple (21-day) ascending-dose study in twenty otherwise-healthy male and female patients with mild-to-moderate major depressive disorder (as defined by the American Psychiatry Association Diagnostic and Statistical Manual of Mental Disorders—4th edition [DSM-IV-TR] and confirmed by the Mini International Neuropsychiatric Interview [MINI]) of mild to moderate severity (as assessed by the Montgomery-Åsberg Depression Rating Scale [MADRS]).

Compositions and Administration

The patients are divided into 2 cohorts. Each cohort has ten members, eight receiving HT-2157 and two receiving a placebo. Patients in cohort 1 are randomized to receive a 125 mg enteric-coated, solid dosage HT-2157 formulation (or matching placebo) on days 1-21 in a fed state, and multiple parameters, including pharmacokinetics (PK), safety, and pharmacodynamics (PD) data are evaluated. Procedures for Cohort 2 are identical to those for Cohort 1, except that patients in Cohort 2 will receive single doses of 250 mg HT-2157 for 21 days.

Cognitive function in Cohorts 1 and 2 is assessed using the CogState testing method, which comprises a customizable range of computerized cognitive tasks able to measure baseline and change in all cognitive domains. Specialized tasks in CogState can assess attention, memory, executive function, as well as language and social-emotional cognition.

Mean blood methemoglobin levels in each Cohort do not increase substantially and do not exceed 1.5% in any single patient as measured daily—even after 21 days of dosing. There is no evidence of hemolytic processes or significant cardiovascular findings. Under the dosing duration of 3 weeks (21 days), there is evidence of HT-2157-induced changes on PD endpoints that indicate an antidepressant effect.

While certain embodiments are described herein, it will be understood that the described embodiments are not intended to limit the scope of the invention as defined by the appended claims. On the contrary, the present disclosure is intended to cover alternatives, modifications and equivalents that may be included within the spirit and scope of the invention as defined by the appended claims. Furthermore, certain details in the present disclosure are provided to convey a thorough understanding of the invention defined by the appended claims. However, it will be apparent to those skilled in the art that certain embodiments may be practiced without these details. In certain instances, well-known methods, procedures, or other specific details have not been described to avoid unnecessarily obscuring aspects of the invention defined by the appended claims.

What is claimed is:

1. A composition comprising a solid-dosage form, wherein said solid-dosage form comprises:
   (a) a therapeutically effective amount of HT-2157 effective for the treatment of a cognitive or nervous system disorder, disease, or condition in a subject, which has the following structure:

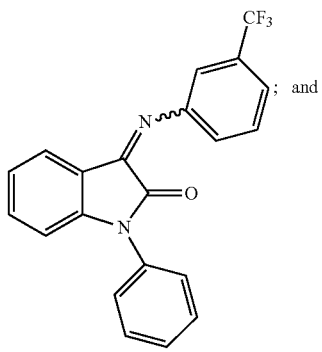

(b) an enteric coating.
2. The composition of claim 1,
   wherein administration of the enteric-coated composition to said subject reduces appearance of clinically relevant methemoglobinemia, relative to administration of a non-enteric coated composition comprising the same amount of HT-2157.
3. The composition of claim 1,
   wherein administration of the enteric-coated composition to said subject results in a lower increase in percent of methemoglobin, relative to administration of a non-enteric coated composition comprising the same amount of HT-2157.
4. The composition of claim 3,
   wherein said administration of the enteric-coated composition increases methemoglobin levels to less than about 3 percent.
5. The composition of claim 3,
   wherein said administration of the enteric-coated composition increases methemoglobin levels to less than about 1.5 percent.
6. The composition of claim 1, wherein the enteric coating comprises a methacrylic polymer.

7. The composition of claim 1, further comprising one or more excipients selected from the following: a diluent, a binder, a surfactant, a glidant, and a lubricant.
8. The composition of claim 1, wherein the composition remains stable after about 1 year of storage at 25° C./60% RH or after about 6 months of storage at 40° C./75% RH.
9. A method of reducing the appearance of clinically relevant methemoglobinemia in a subject, relative to administration of a non-enteric coated composition comprising the same amount of HT-2157, comprising administering to said subject a composition comprising a solid-dosage form, wherein said solid-dosage form comprises:
   (a) a therapeutically effective amount of HT-2157 effective for the treatment of a cognitive or nervous system disorder, disease, or condition in said subject, which has the following structure:

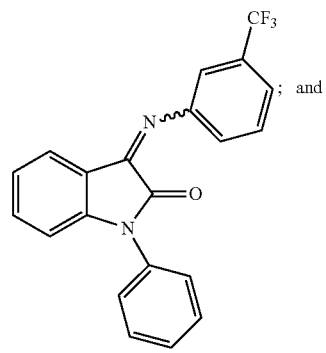

(b) an enteric coating.
10. A method comprising:
   administering a composition comprising a solid-dosage form to a subject, wherein said solid-dosage form comprises:
   (a) a therapeutically effective amount of HT-2157 effective for the treatment of a cognitive or nervous system disorder, disease, or condition in said subject, which has the following structure:

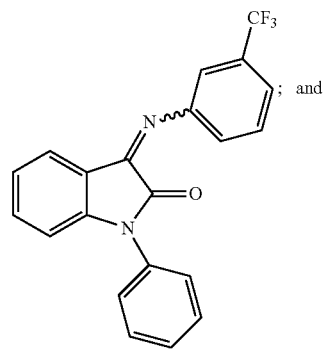

(b) an enteric coating,
   wherein said administering results in a lower increase in percent of methemoglobin, relative to administration of a non-enteric coated composition comprising the same amount of HT-2157.
11. The method of claim 10,
   wherein said administration of the enteric coated composition increases methemoglobin levels to less than about 3 percent.

12. The method of claim 10, wherein said administration of the enteric coated composition increases methemoglobin levels to less than about 1.5 percent.

13. The method of claim 9, wherein the enteric coating of the composition administered in step (a) comprises a methacrylic polymer.

14. The method of claim 9, wherein the composition administered in step (a) further comprises one or more excipients selected from the following: a diluent, a binder, a surfactant, a glidant, and a lubricant.

15. The method of claim 9, wherein the composition administered in step (a) remains stable after about 1 year of storage at 25° C./60% R.H or after about 6 months of storage at 40° C./75% R.H.

16. A method of treating a CNS disorder comprising administering the composition of claim 1 to a subject in need thereof.

17. The method of claim 16, wherein the CNS disorder is depression or anxiety.

18. A method comprising the steps of:
(a) providing cognitive training to an animal in need of treatment of a cognitive impairment under conditions sufficient to produce an improvement in performance by said animal of a cognitive function whose deficit is associated with said cognitive impairment;
(b) administering the composition of claim 1 to said animal in conjunction with said cognitive training;
(c) repeating said providing and said administering of steps (a) and (b) one or more times; and
(d) reducing the number of training sessions sufficient to produce said improvement in performance, relative to the improvement in performance produced by cognitive training alone.

19. The method of claim 18, wherein said administering reduces appearance of clinically relevant methemoglobinemia or results in a lower increase in percent of methemoglobin, relative to administration of a non-enteric coated composition comprising the same amount of HT-2157.

20. The method of claim 18, wherein the cognitive impairment includes a memory impairment.

* * * * *